United States Patent
Wu et al.

(10) Patent No.: US 11,977,232 B2
(45) Date of Patent: May 7, 2024

(54) WEARABLE DEVICE AND METHOD FOR ADJUSTING DISPLAY STATE BASED ON ENVIRONMENT

(71) Applicant: Coretronic Corporation, Hsin-Chu (TW)

(72) Inventors: Shih-Min Wu, Hsinchu (TW); Yi-Fa Wang, Hsinchu (TW); Ping-Chen Ma, Hsinchu (TW)

(73) Assignee: Coretronic Corporation, Hsin-Chu (TW)

( * ) Notice: Subject to any disclaimer, the term of this patent is extended or adjusted under 35 U.S.C. 154(b) by 0 days.

(21) Appl. No.: 17/703,999

(22) Filed: Mar. 25, 2022

(65) Prior Publication Data
US 2022/0342220 A1    Oct. 27, 2022

(30) Foreign Application Priority Data

Apr. 23, 2021  (CN) .......................... 202110441267.4

(51) Int. Cl.
*G02B 27/01*    (2006.01)
*A61B 90/00*    (2016.01)

(52) U.S. Cl.
CPC .......... *G02B 27/0172* (2013.01); *A61B 90/36* (2016.02); *A61B 2090/365* (2016.02); *G02B 2027/0138* (2013.01); *G02B 2027/014* (2013.01); *G02B 27/017* (2013.01)

(58) Field of Classification Search
CPC .............. G02B 27/0172; G02B 27/017; G02B 2027/0138; G02B 2027/014; A61B 90/36; A61B 2090/365; A61B 2090/372; A61B 2090/502; G16H 30/20; G06F 3/14
See application file for complete search history.

(56) References Cited

U.S. PATENT DOCUMENTS

| | | | | |
|---|---|---|---|---|
| 10,366,487 | B2 | 7/2019 | Kim | |
| 2009/0141175 | A1* | 6/2009 | Hsu | H04N 23/88 348/E9.049 |
| 2013/0257691 | A1* | 10/2013 | Saito | H04N 5/445 345/8 |
| 2014/0085203 | A1* | 3/2014 | Kobayashi | G06F 3/012 345/158 |
| 2017/0213377 | A1* | 7/2017 | Torii | H04N 21/47 |

(Continued)

FOREIGN PATENT DOCUMENTS

| | | | | |
|---|---|---|---|---|
| CN | 106371585 | | 2/2017 | |
| CN | 107015361 | A * | 8/2017 | ......... G02B 27/0172 |

(Continued)

OTHER PUBLICATIONS

"Office Action of Taiwan Counterpart Application", dated Sep. 26, 2022, p. 1-p. 9.

*Primary Examiner* — Ricardo Osorio
(74) *Attorney, Agent, or Firm* — JCIPRNET (57) ABSTRACT

A wearable device and a method for adjusting a display state based on an environment are provided. The method is adapted for the wearable device. The method includes: capturing an environmental image; when determining that there is a specific object in the environmental image, determining a display mode of a display circuit based on the specific object; and controlling the display circuit to be adjusted to a display state corresponding to the display mode.

23 Claims, 3 Drawing Sheets

(56) References Cited

U.S. PATENT DOCUMENTS

2019/0096135 A1    3/2019  Dal Mutto et al.
2022/0084287 A1*   3/2022  Sasaki ..................... G06F 3/011
2022/0286655 A1*   9/2022  Hattori ..................... H04N 9/77

FOREIGN PATENT DOCUMENTS

| CN | 107076992 | | 8/2017 | |
| CN | 107810535 A | * | 3/2018 | ............ A61B 5/742 |
| CN | 109144244 | | 1/2019 | |
| CN | 110488969 A | * | 11/2019 | ......... G02B 27/0101 |
| CN | 110708533 A | * | 1/2020 | |
| JP | 2014039116 A | * | 2/2014 | |
| JP | 2018033111 A | * | 3/2018 | ......... G02B 27/0172 |
| TW | 201728961 | | 8/2017 | |
| TW | I670520 | | 9/2019 | |
| WO | WO-2018131238 A1 | * | 7/2018 | ............ G06T 19/00 |

* cited by examiner

WEARABLE DEVICE AND METHOD FOR ADJUSTING DISPLAY STATE BASED ON ENVIRONMENT

CROSS-REFERENCE TO RELATED APPLICATION

This application claims the priority benefit of China application serial no. 202110441267.4 filed on Apr. 23, 2021. The entirety of the above-mentioned patent application is hereby incorporated by reference herein and made a part of this specification.

BACKGROUND

Technical Field

The invention relates to a technology for adjusting a display state, and particularly relates to a wearable device and a method for adjusting a display state based on an environment.

Description of Related Art

In the prior art, an augmented reality (AR) device may adjust a display state (such as a brightness, etc.) of the AR device after sensing an environmental brightness through a light sensor. Generally, the higher the environmental brightness is, the higher the display brightness of the AR device is adjusted, and vice versa.

However, when the light sensor on the AR device cannot correctly detect the environmental brightness due to blocking of a light source, etc., the AR device may probably adjust the brightness to relatively inappropriate display brightness accordingly (for example, to present an excessively low brightness in a brighter environment), resulting in poor user experience.

The information disclosed in this Background section is only for enhancement of understanding of the background of the described technology and therefore it may contain information that does not form the prior art that is already known to a person of ordinary skill in the art. Further, the information disclosed in the Background section does not mean that one or more problems to be resolved by one or more embodiments of the invention were acknowledged by a person of ordinary skill in the art.

SUMMARY

The invention is directed to a wearable device and a method for adjusting a display state based on an environment, which are adapted to resolve the technical problem.

Other objects and advantages of the invention may be further illustrated by the technical features broadly embodied and described as follows.

In order to achieve one or a portion of or all of the objects or other objects, an embodiment of the invention provides a wearable device including an image capturing circuit, a storage circuit, a display circuit and a processor. The storage circuit stores a program code. The processor is coupled to the image capturing circuit, the storage circuit and the display circuit, and accesses the program code. The processor controls the image capturing circuit to capture an environmental image. When determining that there is at least one specific object in the environmental image, the processor determines a display mode of the display circuit based on the at least one specific object, and the processor controls the display circuit to be adjusted to a display state corresponding to the display mode.

In order to achieve one or a portion of or all of the objects or other objects, an embodiment of the invention provides a method for adjusting a display state based on an environment, which is adapted to a wearable device including an image capturing circuit and a display circuit. The method includes: controlling the image capturing circuit to capture an environmental image; when determining that there is at least one specific object in the environmental image, determining a display mode of the display circuit based on the at least one specific object; and controlling the display circuit to be adjusted to a display state corresponding to the display mode.

Based on the above description, the embodiments of the invention have at least one of following advantages or effects. In the embodiments of the invention, the method of adjusting a display state based on environment of the invention is adapted to determine the display mode of the display circuit according to the specific object in the environmental image captured by the wearable device of the invention, so that the display state of the display circuit may be more suitable for the environment where the wearable device is located. Compared with the method of adjusting a display brightness only based on measured ambient light, the invention may appropriately determine the display mode of the display circuit, thereby improving the use experience of the wearable device.

Other objectives, features and advantages of the invention will be further understood from the further technological features disclosed by the embodiments of the invention wherein there are shown and described preferred embodiments of this invention, simply by way of illustration of modes best suited to carry out the invention.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

It is to be understood that other embodiment may be utilized and structural changes may be made without departing from the scope of the invention. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings.

In the following detailed description of the preferred embodiments, reference is made to the accompanying drawings which form a part hereof, and in which are shown by way of illustration specific embodiments in which the invention may be practiced. In this regard, directional terminology, such as "top," "bottom," "left," "right," "front," "back," etc., is used with reference to the orientation of the Figure(s) being described and are not intended to be limiting of the invention.

Figure 1:
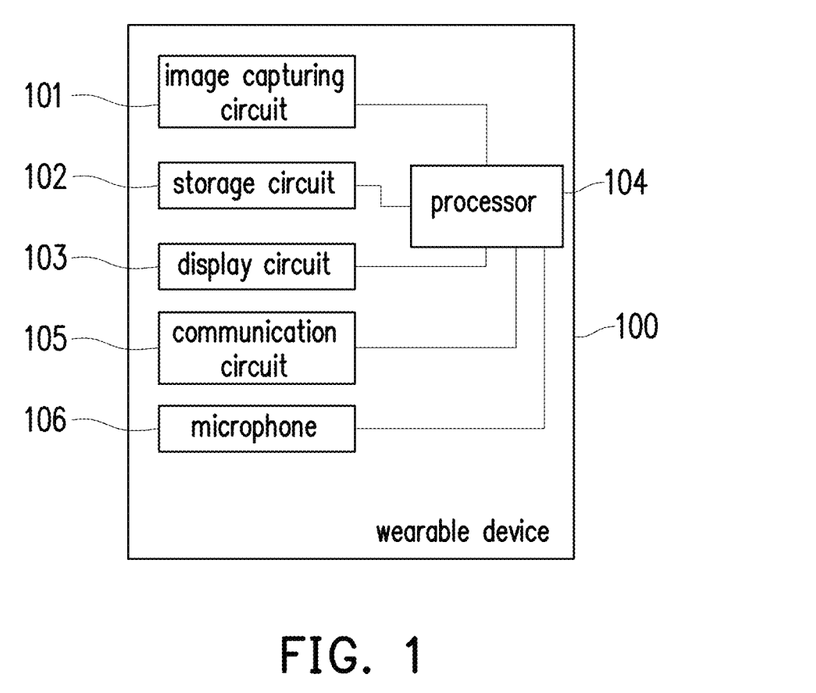
FIG. 1 is a schematic diagram of a wearable device according to an embodiment of the invention.

Referring to FIG. 1, FIG. 1 is a schematic diagram of a wearable device according to an embodiment of the invention. In different embodiments, the wearable device 100 is, for example, a pair of augmented reality (AR) glasses or other wearable devices with a display function, but the invention is not limited thereto.

As shown in FIG. 1, the wearable device 100 includes an image capturing circuit 101, a storage circuit 102, a display circuit 103 and a processor 104.

The image capturing circuit 101 is, for example, any image capturing device with elements such as a charge coupled device (CCD) lens, a complementary metal oxide semiconductor transistor (CMOS) lens, etc., but the invention is not limited thereto.

The storage circuit 102 is, for example, any type of a fixed or removable random access memory (RAM), a read-only memory (ROM), a flash memory, a hard disk or other similar devices or a combination of these devices, which may be used to record a plurality of program codes or modules.

The display circuit 103 may include, for example, a display (for example, a transmissive display) of the wearable device 100 and related control circuits (for example, a backlight module, an optical engine, etc.), but the invention is not limited thereto.

The processor 104 is coupled to the image capturing circuit 101, the storage circuit 102, and the display circuit 103, and may be a general purpose processor, a special purpose processor, a conventional processor, a digital signal processor, a plurality of microprocessors, one or a plurality of microprocessors combined with a digital signal processor core, a controller, a microcontroller, an application specific integrated circuit (ASIC), a field programmable gate array (FPGA), any other types of integrated circuits, state machines, processors based on advanced RISC machine (ARM) and similar products.

In an embodiment of the invention, the processor 104 may access the modules and program codes recorded in the storage circuit 102 to implement the method for adjusting a display state based on an environment provided by the invention, and details thereof are described below.

Figure 2:
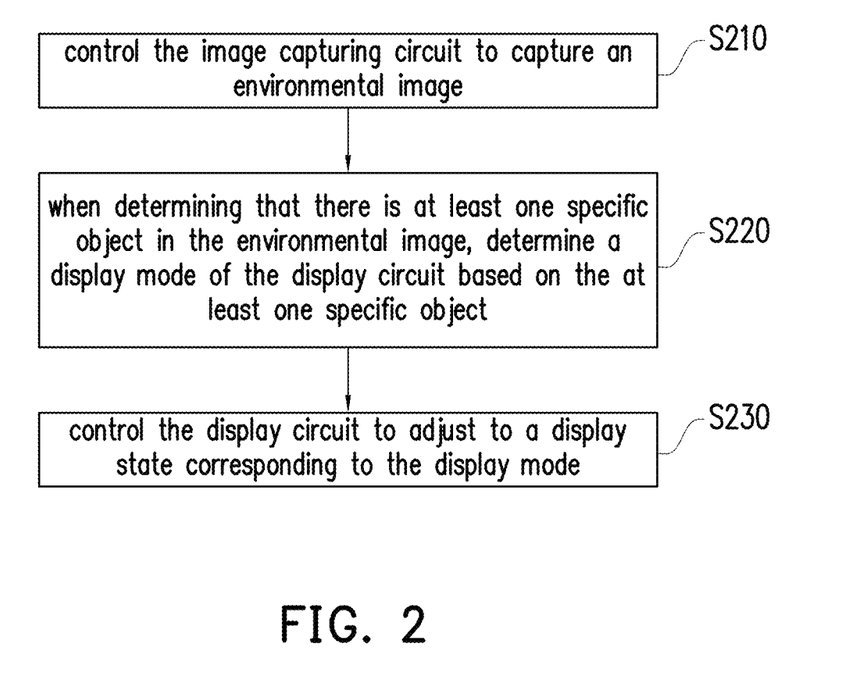
FIG. 2 is a flowchart of a method for adjusting a display state based on an environment according to an embodiment of the invention.

Referring to FIG. 2, FIG. 2 is a flowchart of a method for adjusting a display state based on an environment according to an embodiment of the invention. The method of the embodiment may be executed by the wearable device 100 in FIG. 1, and various steps of FIG. 2 are described in detail below with reference of the components shown in FIG. 1.

First, in step S210, the processor 104 may control the image capturing circuit 101 to capture an environmental image. In different embodiments, the processor 104 may control the image capturing circuit 101 to shoot toward the front of the wearable device 100 (which may correspond to the front of the user) or any other directions to obtain an image to serve as the environmental image, but the invention is not be limited thereto.

In step S220, when it is determined that there is a specific object in the environmental image, the processor 104 may determine a display mode of the display circuit 103 based on the specific object, and control the display circuit 103 to be adjusted to a display state corresponding to the display mode in step S230.

In detail, in certain specific environments, certain objects are almost bound to exist. For example, various surgical appliances (for example, scalpels) and surgical devices (for example, operating tables, etc.) may almost certainly appear in operating rooms, and theater seats and theater screens may almost certainly appear in movie theaters.

Therefore, in an embodiment, after obtaining the aforementioned environmental image, the processor 104 may determine whether there is a specific object in the environmental image. When the processor 104 determines that certain objects (such as scalpels, an operating table, etc.) appear in the environmental image, it means that the wearable device 100 is currently in the corresponding environment (such as an operating room). Since different environments should be suitable for different display states, the wearable device 100 may be pre-stored with a plurality of predetermined display modes corresponding to the different environments, so that when it is determined that the wearable device 100 is in one of the above environments, the corresponding predetermined display mode is selected as the display mode of the display circuit 103 to adjust the display state of the display circuit 103.

In an embodiment, the invention may determine whether there is the specific object in the obtained environmental image by using a following mechanism. Generally, the storage circuit 102 may store one or a plurality of pre-stored images corresponding to various types of specific objects, and the processor 104 may execute a key point extraction algorithm on these pre-stored images to obtain a plurality of key points of each specific object. Similarly, the processor 104 may execute the key point extraction algorithm on the aforementioned environmental image (which may include one or a plurality of environmental objects) to obtain a plurality of key points of each environmental object. Thereafter, the processor 104 may individually compare the key points of each environmental object and the aforementioned specific object. If the processor 104 determines that the key points of one of the environmental objects correspond to the key points of a certain specific object, the processor 104 may determine that the environmental object corresponds to the specific object, but the invention is not limited thereto.

For example, it is assumed that the storage circuit 102 stores a first pre-stored image of a first specific object (such as a scalpel) in the above specific objects. In an embodiment, the processor 104 may execute the key point extraction algorithm on the environmental image to obtain a plurality key points of each environmental object, where the environmental objects may include a first environmental object.

In addition, the processor 104 may also execute the aforementioned key point extraction algorithm on the first pre-stored image of the first specific object to obtain a plurality of first key points of the first specific object. Thereafter, the processor 104 may determine whether the aforementioned key points of the first environmental object correspond to the aforementioned first key points of the first specific object.

If yes, the processor 104 may determine that the first environmental object is the first specific object (i.e., the first environmental object is a scalpel), and otherwise may determine that the first environmental object is not the first specific object, and may continue to compare the first key points of the first environmental object with the key points of other specific objects in the aforementioned specific objects, but the invention is not limited thereto.

Figure 3:
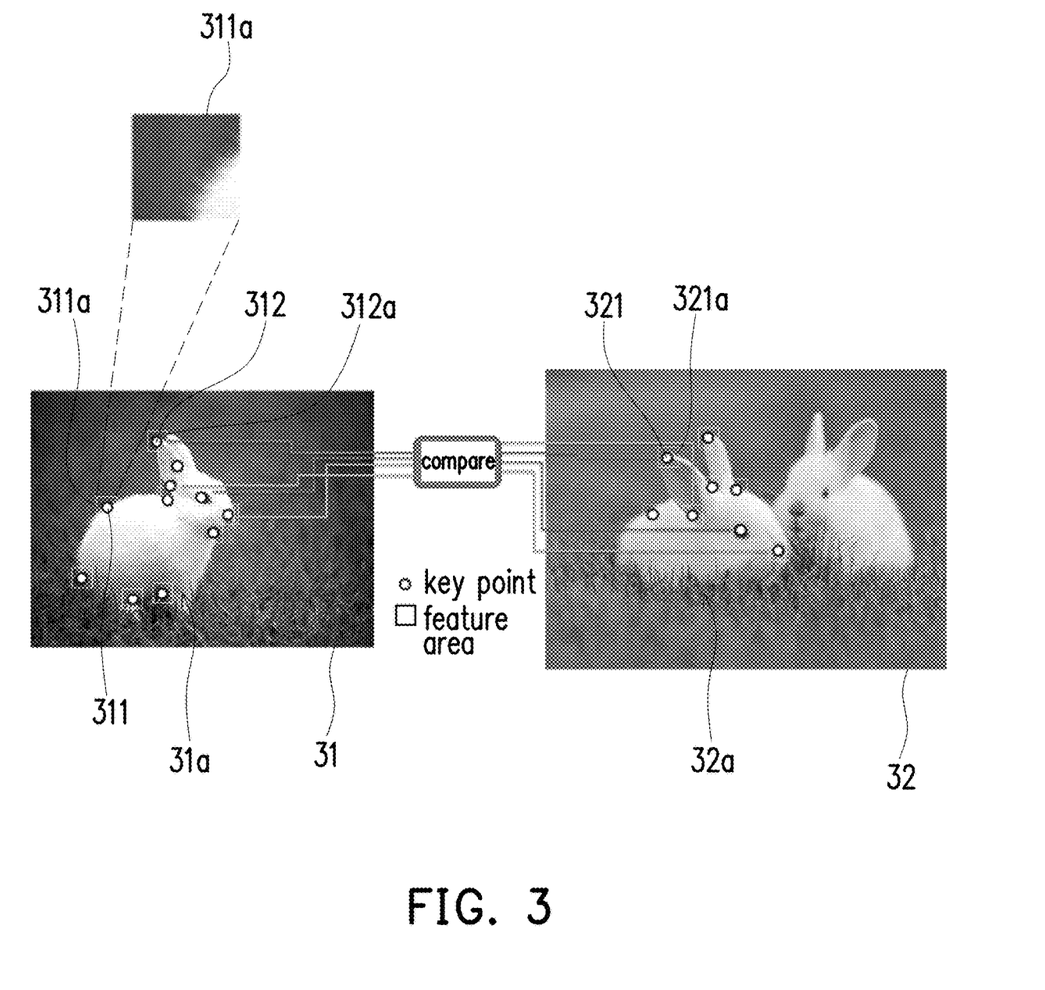
FIG. 3 is a schematic diagram of a key point comparison mechanism according to an embodiment of the invention.

In an embodiment, the processor 104 may determine whether the key points of the specific object correspond to the key points of the environmental object based on the mechanism shown in FIG. 3, but the invention is not limited thereto.

Referring to FIG. 3, FIG. 3 is a schematic diagram of a key point comparison mechanism according to an embodiment of the invention. In FIG. 3, it is assumed that a considered specific object 31a is a rabbit, the storage circuit 102 may store a pre-stored image 31 of the specific object 31a. In this case, the processor 104 may execute the key point extraction algorithm on the pre-stored image 31 to obtain a plurality of key points (which are respectively shown as a circle) of the specific object 31a. Thereafter, the processor 104 may extract a feature area (shown as a rectangular frame) of each key point and record it as a reference for subsequent comparison.

For example, after the processor 104 obtains a key point 311 belonging to the specific object 31a in the pre-stored image 31, the processor 104 may, for example, take the key point 311 as a center, and extract an image area with a predetermined size from the pre-stored image 31 to serve as a feature area 311a of the key point 311 for recording. Similarly, after the processor 104 obtains a key point 312 belonging to the specific object 31a in the pre-stored image 31, the processor 104 may, for example, take the key point 312 as a center, and extract an image area with a predetermined size from the pre-stored image 31 to serve as a feature area 312a of the key point 312 for recording, but the invention is not limited thereto.

In FIG. 3, it is assumed that an environmental image 32 obtained by the processor 104 includes an environmental object 32a, the processor 104 may execute the key point extraction algorithm on the environmental image 32 to obtain the key points and the corresponding feature areas (for example, the key point 321 and the corresponding feature area 321a) of each environmental object (for example, the environmental object 32a) in the environmental image 32.

In the embodiment, the processor 104 may determine whether the key points of the specific object 31a match the key points of the environmental object 32a. In FIG. 3, it is assumed that the processor 104 determines that the feature area 312a of the key point 312 of the specific object 31a matches the feature area 321a of the key point 321 of the environmental object 32a, the processor 104 may determine that the key point 312 of the specific object 31a matches the key point 321 of the environmental object 32a.

In an embodiment, when determining that there are N key points in the environmental object 32a that match the key points of the specific object 31a, the processor 104 may determine that the key points of the specific object 31a correspond to the key points of the environmental object 32a, but the invention is not limited thereto.

In FIG. 3, it is assumed that N is set to 4, after determining that there are 4 key points in the environmental object 32a that match the key points of the specific object 31a (for example, the 4 pairs of key points connected by line segments in FIG. 3), the processor 104 may determine that the key points of the specific object 31a correspond to the key points of the environmental object 32a. In this case, the processor 104 may determine that the environmental object 32a in the environmental image 32 is the specific object 31a (i.e., the rabbit), but the invention is not limited thereto.

After finding out each specific object in the environmental image according to the above teaching, the processor 104 may accordingly determine the display mode of the display circuit 103. For the convenience of description, it is assumed that the wearable device 100 may be pre-stored with pre-determined display modes such as a first display mode (a corresponding environment thereof is, for example, an operating room) and a second display mode (which, for example, corresponds to a reading environment room), but the invention it is not limited thereto.

In an embodiment, when the processor 104 determines that one or a plurality of specific objects in the environmental image all correspond to the aforementioned first display mode, the processor 104 may determine that the display mode of the display circuit 103 is the first display mode. For example, it is assumed that the processor 104 determines that the environment image includes two specific objects: a scalpel and an operating table, which means that the wearable device 100 is located in the operating room at the moment. In this case, the processor 104 may select the first display mode corresponding to the operating room as the display mode of the display circuit 104.

For another example, it is assumed that the processor 104 determines that the environment image includes three specific objects including a book, stationery, and a sentence, which means that the wearable device 100 should be in a reading environment at the moment. In this case, the processor 104 may select the second display mode corresponding to the reading environment as the display mode of the display circuit 104.

In some embodiments, when the processor 104 determines that the specific objects in the environment image include one or a plurality of first objects corresponding to the first display mode and one or a plurality of second objects corresponding to the second display mode, the processor 104 may obtain a first quantity of the above first objects and a second quantity of the above second objects, and compare the first quantity with the second quantity.

In an embodiment, when it is determined that the first quantity of the first objects is greater than the second quantity of the second objects, the processor 104 may determine the display mode of the display circuit 103 to be the first display mode. On the other hand, when it is determined that the first quantity of the first objects is less than the second quantity of the second objects, the processor 104 may determine the display mode of the display circuit 103 to be the second display mode.

For example, it is assumed that the processor 104 determines that the environmental image includes three specific objects such as a scalpel corresponding to the first display mode, operating tables (i.e., the first object), and a book (i.e., the second object) corresponding to the second display mode. In this case, since a quantity of the first objects (i.e., 2) is greater than a quantity of the second objects (i.e., 1), the processor 104 may determine that the display mode of the display circuit 103 is the first display mode, but the invention is not limited thereto.

For another example, it is assumed that the processor 104 determines that the environmental image includes five specific objects such as a scalpel corresponding to the first display mode, operating tables (i.e., the first object), and a book, stationary, a sentence (i.e., the second objects) corresponding to the second display mode. In this case, since a quantity of the first objects (i.e., 2) is greater than a quantity of the second objects (i.e., 3), the processor 104 may determine that the display mode of the display circuit 103 is the second display mode, but the invention is not limited thereto.

In different embodiments, the wearable device 100 of the invention may be, for example, pre-stored with predetermined display modes such as a medical operation mode (a corresponding environment thereof is, for example, an operating room), a reading mode (which, for example, corresponds to a reading environment), a movie viewing mode (which, for example, corresponds to a theater environment), etc., but the invention is not limited thereto.

In an embodiment, the specific objects corresponding to the medical operation mode may include, for example, various surgical tools and/or surgical devices. Therefore, when the processor 104 determines that (most of) the specific objects in the environmental image belong to the surgical tools and/or the surgical devices, the processor 104 may determine the medical operation mode as the display mode of the display circuit 103, and may control the display circuit 103 to be adjusted to the display state corresponding to the medical operation mode.

Figure 4:
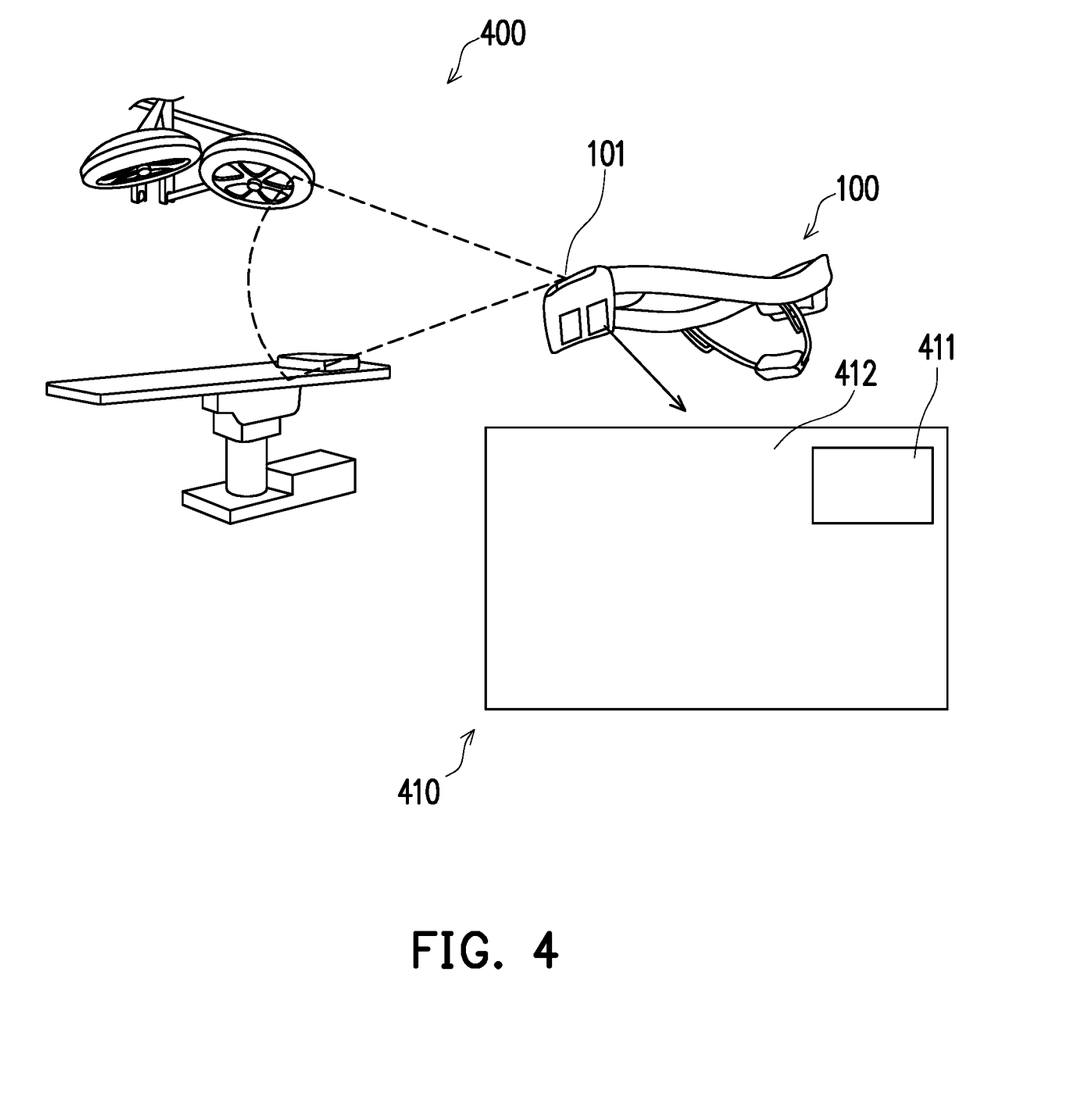
FIG. 4 is a schematic diagram of a display state corresponding to a medical operation mode according to an embodiment of the invention.

Referring to FIG. 4, FIG. 4 is a schematic diagram of the display state corresponding to the medical operation mode according to an embodiment of the invention. In the embodiment, it is assumed that the wearable device 100 is located in an environment 400 (for example, an operating room), after the image capturing circuit 101 captures the environmental image, the processor 104 may select the medical operation mode as the display mode of the display circuit 103 by determining that there are various surgical tools/ surgical devices in the environmental image.

In FIG. 4, the processor 104 may adjust the display interface 410 of the display circuit 103 to a picture-in-picture image, where a sub-picture 411 in the picture-in-picture image may display surgical information, and a main picture 412 of the picture-in-picture image may be a visually transparent image, so as to facilitate a user (for example, a doctor) to confirm a situation of the operating room in a visual manner, but the invention is not limited thereto.

Moreover, the processor 104 may also adjust a brightness and a color temperature of the display interface to a first specified brightness and a first specified color temperature corresponding to the medical operation mode, but the invention is not limited thereto.

In an embodiment, the specific objects corresponding to the reading mode may, for example, include various books, stationery and/or sentences. Therefore, when the processor 104 determines that (most of) the specific objects in the environmental image belong to various books, stationery and/or sentences, the processor 104 may determine the reading mode as the display mode of the display circuit 103, and may control the display circuit 103 to be adjusted to the display state corresponding to the reading mode. For example, the processor 104 may adjust the brightness and color temperature of the display interface of the display circuit 103 to a second specified brightness (which may be lower than the first specified brightness) and a second specified color temperature corresponding to the reading mode, but the invention is not limited thereto.

In an embodiment, the specific objects corresponding to the viewing mode may include, for example, various theater seats, a theater screen or various articles that may appear in a theater, but the invention is not limited thereto. Therefore, when the processor 104 determines that (most of) the specific objects in the environmental image belong to various theater seats and/or theater screen, the processor 104 may determine the movie viewing mode as the display mode of the display circuit 103, and may control the display circuit 103 to be adjusted to the display state corresponding to the movie viewing mode. For example, the processor 104 may, for example, adjust the display interface of the display circuit 103 to a visually transparent image, and adjust the brightness and color temperature of the display interface of the display circuit 103 to a third specified brightness (which may be lower than the second specified brightness) and a third specified color temperature corresponding to the movie viewing mode, but the invention is not limited thereto.

In an embodiment, it is assumed that the theater screen is used to play specific visual content (such as a movie), the processor 104 may also obtain subtitles corresponding to the specific visual content and control the display circuit 103 to display the subtitles in the display interface. In an embodiment, the subtitles may be, for example, displayed at a bottom of the display interface. In this case, the display interface may be a visually transparent image except for a subtitle area, but the invention limited thereto.

In different embodiments, the above subtitles may be presented in any language, such as original subtitles or subtitles translated into a language familiar to the user, which is not limited by the invention. In some embodiments, the wearable device 100 may further include a communication circuit 105 (which is, for example, a wireless network module) coupled to the processor 104, and the processor 104 may control the communication circuit 105 to download subtitles corresponding to the above specific visual content, but the invention is not limited thereto.

In an embodiment, the wearable device 100 may also include a microphone 106 coupled to the processor 104, and the processor 104 may control the microphone 106 to receive audio content (for example, sounds/sound effects of a movie, etc.) corresponding to the above specific visual content. Then, the processor 104 may translate the received audio content into subtitles corresponding to the specific visual content in real-time and present the subtitles in the display interface, but the invention is not limited thereto.

In some embodiments, since the display mode automatically determined by the processor 104 based on the specific objects in the environmental image may not necessarily meet the needs of the user, the invention further provides a mechanism that allows the user to specify other display modes orally, and details thereof are as follows.

In an embodiment, it is assumed that the processor 104 has selected the first display mode based on the specific objects in the environmental image. In this case, the processor 104 may additionally control the microphone 105 to receive a voice signal. In the embodiment, the voice signal may, for example, include one of the predetermined display modes specified by the user orally, but the invention is not limited thereto.

For ease of understanding, it is assumed that the user orally specifies the second display mode as the display mode of the display circuit 103. In this case, when it is determined that the voice signal indicates the second display mode as the display mode of the display circuit 103, the processor 104 may control the display circuit 103 to display a confirmation message, where the confirmation message may include a first option and a second option respectively corresponding to the first display mode and the second display mode.

Correspondingly, the user may select the required one of the first option and the second option as the display mode of the display circuit 103. In an embodiment, when it is determined that the first option is selected, the processor 104 may control the display circuit 103 to be adjusted to the display state corresponding to the first display mode. On the other hand, when it is determined that the second option is selected, the processor 104 may control the display circuit 103 to be adjusted to the display state corresponding to the second display mode.

For example, it is assumed that the processor 104 selects the medical operation mode based on the specific objects in the environmental image, but the voice signal provided by the user indicates that the user wants to select the movie viewing mode. In this case, the processor 104 may control the display circuit 103 to display a confirmation message, which may include a first option corresponding to the medical operation mode and a second option corresponding to the movie viewing mode for the user to select.

It is assumed that the user selects the first option corresponding to the medical operation mode in the above confirmation message, the processor 104 may control the display circuit 103 to be adjusted to the display state corresponding to the medical operation mode (for example, to adjust the display interface to a picture-in-picture image, etc.). On the other hand, if the user selects the second option corresponding to the movie viewing mode in the above confirmation message, the processor 104 may control the display circuit 103 to be adjusted to the display state corresponding to the movie viewing mode (for example, to adjust the display interface to a visually transparent image, etc.), but the invention is not limited thereto.

In summary, the method of adjusting a display state based on environment of the invention is adapted to determine the display mode of the display circuit according to the specific object in the environmental image captured by the wearable device of the invention, so that the display state of the display circuit may be more suitable for the environment where the wearable device is located. Compared with the method of adjusting a display brightness only based on measured ambient light, the invention may appropriately determine the display mode of the display circuit, thereby improving the use experience of the wearable device.

It will be apparent to those skilled in the art that various modifications and variations can be made to the disclosed embodiments without departing from the scope or spirit of the invention. In view of the foregoing, it is intended that the invention covers modifications and variations provided they fall within the scope of the following claims and their equivalents. Moreover, any embodiment of or the claims of the invention is unnecessary to implement all advantages or features disclosed by the invention. Moreover, the abstract and the name of the invention are only used to assist patent searching, and are not used to limit a protection range of the invention. Moreover, "first", "second", etc. mentioned in the specification and the claims are merely used to name the elements and should not be regarded as limiting the upper or lower bound of the number of the components/devices.

The foregoing description of the preferred embodiments of the invention has been presented for purposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to best explain the principles of the invention and its best mode practical application, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Therefore, the term "the invention", "the present invention" or the like does not necessarily limit the claim scope to a specific embodiment, and the reference to particularly preferred exemplary embodiments of the invention does not imply a limitation on the invention, and no such limitation is to be inferred. The invention is limited only by the spirit and scope of the appended claims. Moreover, these claims may refer to use "first", "second", etc. following with noun or element. Such terms should be understood as a nomenclature and should not be construed as giving the limitation on the number of the elements modified by such nomenclature unless specific number has been given. The abstract of the disclosure is provided to comply with the rules requiring an abstract, which will allow a searcher to quickly ascertain the subject matter of the technical disclosure of any patent issued from this disclosure. It is submitted with the understanding that it will not be used to interpret or limit the scope or meaning of the claims. Any advantages and benefits described may not apply to all embodiments of the invention. It should be appreciated that variations may be made in the embodiments described by persons skilled in the art without departing from the scope of the invention as defined by the following claims. Moreover, no element and component in the disclosure is intended to be dedicated to the public regardless of whether the element or component is explicitly recited in the following claims.

What is claimed is:

1. A wearable device, comprising:
    an image capturing circuit;
    a storage circuit, storing a program code;
    a display circuit; and
    a processor, coupled to the image capturing circuit, the storage circuit, and the display circuit, and configured to access the program code, wherein the processor is configured to control the image capturing circuit to capture an environmental image, wherein when the processor determines that there is at least one specific object in the environmental image, the processor is configured to determine a display mode of the display circuit based on the at least one specific object, and the processor is configured to control the display circuit to be adjusted to a display state corresponding to the display mode,
    wherein the at least one specific object comprises at least one of a surgical tool and a surgical device, and the processor is adapted to execute:
    determining the display mode of the display circuit to be a medical operation mode, and controlling the display circuit to be adjusted to a display state corresponding to the medical operation mode, comprising adjusting a display interface of the display circuit to a picture-in-picture image, wherein a sub-picture in the picture-in-picture image displays surgery information, and a main picture of the picture-in-picture image is a visually transparent image.

2. The wearable device as claimed in claim 1, wherein the display state corresponding to the medical operation mode is adjusting a brightness and a color temperature of the display interface to a first specified brightness and a first specified color temperature corresponding to the medical operation mode.

3. The wearable device as claimed in claim 1, wherein the wearable device further comprises a pair of augmented reality glasses.

4. The wearable device as claimed in claim 1, wherein the processor is adapted to execute: when determining that the at least one specific object corresponds to a first display mode in a plurality of predetermined display modes, determining the display mode of the display circuit to be the first display mode.

5. A wearable device, comprising:
an image capturing circuit;
a storage circuit, storing a program code;
a display circuit; and
a processor, coupled to the image capturing circuit, the storage circuit, and the display circuit, and configured to access the program code, wherein the processor is configured to control the image capturing circuit to capture an environmental image, wherein when the processor determines that there is at least one specific object in the environmental image, the processor is configured to determine a display mode of the display circuit based on the at least one specific object, and the processor is configured to control the display circuit to be adjusted to a display state corresponding to the display mode,
wherein the storage circuit stores a first pre-stored image of a first specific object in the at least one specific object, there is at least one environmental object in the environmental image, and the processor is adapted to execute:
executing a key point extraction algorithm on the environmental image to obtain a plurality of key points of each of the at least one environmental object, wherein the at least one environmental object comprises a first environmental object;
executing the key point extraction algorithm on the first pre-stored image to obtain a plurality of first key points of the first specific object; and
when determining that the key points of the first environmental object correspond to the first key points of the first specific object, determining the first environmental object to be the first specific object.

6. A wearable device, comprising:
an image capturing circuit;
a storage circuit, storing a program code;
a display circuit; and
a processor, coupled to the image capturing circuit, the storage circuit, and the display circuit, and configured to access the program code, wherein the processor is configured to control the image capturing circuit to capture an environmental image, wherein when the processor determines that there is at least one specific object in the environmental image, the processor is configured to determine a display mode of the display circuit based on the at least one specific object, and the processor is configured to control the display circuit to be adjusted to a display state corresponding to the display mode,
wherein the processor is adapted to execute:
when determining that the at least one specific object corresponds to a first display mode in a plurality of predetermined display modes, determining the display mode of the display circuit to be the first display mode,
wherein the predetermined display modes further comprise a second display mode, and the processor is further adapted to execute:
when determining that the at least one specific object comprises at least one first object corresponding to the first display mode and at least one second object corresponding to the second display mode, obtaining a first quantity of the at least one first object and a second quantity of the at least one second object; and
when determining that the first quantity of the at least one first object is greater than the second quantity of the at least one second object, determining the display mode of the display circuit to be the first display mode; and
when determining that the first quantity of the at least one first object is less than the second quantity of the at least one second object, determining the display mode of the display circuit to be the second display mode.

7. A wearable device, comprising:
an image capturing circuit;
a storage circuit, storing a program code;
a display circuit; and
a processor, coupled to the image capturing circuit, the storage circuit, and the display circuit, and configured to access the program code, wherein the processor is configured to control the image capturing circuit to capture an environmental image, wherein when the processor determines that there is at least one specific object in the environmental image, the processor is configured to determine a display mode of the display circuit based on the at least one specific object, and the processor is configured to control the display circuit to be adjusted to a display state corresponding to the display mode,
wherein the at least one specific object comprises at least one of a book, stationery, and a sentence, and the processor is adapted to execute:
determining the display mode of the display circuit to be a reading mode, and controlling the display circuit to be adjusted to a display state corresponding to the reading mode, wherein the display state corresponding to the reading mode is adjusting a brightness and a color temperature of a display interface to a second specified brightness and a second specified color temperature corresponding to the reading mode.

8. A wearable device, comprising:
an image capturing circuit;
a storage circuit, storing a program code;
a display circuit; and
a processor, coupled to the image capturing circuit, the storage circuit, and the display circuit, and configured to access the program code, wherein the processor is configured to control the image capturing circuit to capture an environmental image, wherein when the processor determines that there is at least one specific object in the environmental image, the processor is configured to determine a display mode of the display circuit based on the at least one specific object, and the processor is configured to control the display circuit to be adjusted to a display state corresponding to the display mode,
wherein the at least one specific object comprises at least one of a theater seat and a theater screen, and the processor is adapted to execute:
determining the display mode of the display circuit to be a movie viewing mode, and controlling the display circuit to be adjusted to a display state corresponding to the movie viewing mode, wherein the display state corresponding to the movie viewing mode is adjusting a display interface of the display circuit to a visually transparent image, and adjusting a brightness and a color temperature of the display interface to a third specified brightness and a third specified color temperature corresponding to the movie viewing mode.

9. The wearable device as claimed in claim 8, wherein the theater screen is used for playing specific visual content, and the processor is further adapted to execute:

obtaining at least one subtitle corresponding to the specific visual content, and controlling the display circuit to display the at least one subtitle.

10. The wearable device as claimed in claim 8, further comprising a microphone coupled to the processor, wherein the theater screen is used for playing specific visual content, and the processor is further adapted to execute:

controlling the microphone to receive audio content corresponding to the specific visual content, and translating the audio content into at least one subtitle corresponding to the specific visual content.

11. The wearable device as claimed in claim 8, further comprising a communication circuit coupled to the processor, wherein the theater screen is used for playing specific visual content, and the processor is further adapted to execute:

controlling the communication circuit to download at least one subtitle corresponding to the specific visual content.

12. A wearable device, comprising:
an image capturing circuit;
a storage circuit, storing a program code;
a display circuit; and
a processor, coupled to the image capturing circuit, the storage circuit, and the display circuit, and configured to access the program code, wherein the processor is configured to control the image capturing circuit to capture an environmental image, wherein when the processor determines that there is at least one specific object in the environmental image, the processor is configured to determine a display mode of the display circuit based on the at least one specific object, and the processor is configured to control the display circuit to be adjusted to a display state corresponding to the display mode,
further comprising a microphone coupled to the processor, and the processor is further adapted to execute:
when determining that the display mode of the display circuit is determined to be a first display mode in a plurality of predetermined display modes, controlling the microphone to receive a voice signal;
when determining that the voice signal indicates using a second display mode of the predetermined display modes as the display mode of the display circuit, controlling the display circuit to display a confirmation message, wherein the confirmation message comprises a first option and a second option respectively corresponding to the first display mode and the second display mode;
when determining that the first option is selected, controlling the display circuit to be adjusted to a display state corresponding to the first display mode; and
when determining that the second option is selected, controlling the display circuit to be adjusted to the display state corresponding to the second display mode.

13. A method for adjusting a display state based on an environment, adapted for a wearable device comprising an image capturing circuit and a display circuit, the method comprising:

controlling the image capturing circuit to capture an environmental image;

when determining that there is at least one specific object in the environmental image, determining a display mode of the display circuit based on the at least one specific object; and controlling the display circuit to be adjusted to a display state corresponding to the display mode, wherein the at least one specific object comprises at least one of a surgical tool and a surgical device, and the step of determining the display mode of the display circuit based on the at least one specific object comprises:

determining the display mode of the display circuit to be a medical operation mode, and controlling the display circuit to be adjusted to a display state corresponding to the medical operation mode, comprising adjusting a display interface to a picture-in-picture image, wherein a sub-picture in the picture-in-picture image displays surgery information, and a main picture of the picture-in-picture image is a visually transparent image.

14. The method for adjusting the display state based on the environment as claimed in claim 13, wherein the wearable device stores a first pre-stored image of a first specific object in the at least one specific object, there is at least one environmental object in the environmental image, and the method comprises:

executing a key point extraction algorithm on the environmental image to obtain a plurality of key points of each of the at least one environmental object, wherein the at least one environmental object comprises a first environmental object;

executing the key point extraction algorithm on the first pre-stored image to obtain a plurality of first key points of the first specific object; and when determining that the key points of the first environmental object correspond to the first key points of the first specific object, determining the first environmental object to be the first specific object.

15. The method for adjusting the display state based on the environment as claimed in claim 13, further comprising:
adjusting a brightness and a color temperature of the display interface into a first specified brightness and a first specified color temperature corresponding to the medical operation mode.

16. The method for adjusting the display state based on the environment as claimed in claim 13, wherein the at least one specific object comprises at least one of a book, stationery, and a sentence, and the step of determining the display mode of the display circuit based on the at least one specific object comprises:

determining the display mode of the display circuit to be a reading mode, and controlling the display circuit to be adjusted to a display state corresponding to the reading mode, wherein the display state corresponding to the reading mode comprises is adjusting a brightness and a color temperature of the display interface to a second specified brightness and a second specified color temperature corresponding to the reading mode.

17. The method for adjusting the display state based on the environment as claimed in claim 13, wherein the at least one specific object comprises at least one of a theater seat and a theater screen, and the step of determining the display mode of the display circuit based on the at least one specific object comprises:

determining the display mode of the display circuit to be a movie viewing mode, and controlling the display circuit to be adjusted to a display state corresponding to the movie viewing mode, wherein the display state corresponding to the movie viewing mode is adjusting the display interface to a visually transparent image, and adjusting a brightness and a color temperature of the display interface to a third specified brightness and a third specified color temperature corresponding to the movie viewing mode.

18. The method for adjusting the display state based on the environment as claimed in claim 17, wherein the theater screen is used for playing specific visual content, and the method further comprises:
obtaining at least one subtitle corresponding to the specific visual content, and controlling the display circuit to display the at least one subtitle.

19. The method for adjusting the display state based on the environment as claimed in claim 17, wherein the theater screen is used for playing specific visual content, and the method further comprises:
controlling a microphone of the wearable device to receive audio content corresponding to the specific visual content, and translating the audio content into at least one subtitle corresponding to the specific visual content.

20. The method for adjusting the display state based on the environment as claimed in claim 17, wherein the theater screen is used for playing specific visual content, and the method further comprises:
controlling a communication circuit of the wearable device to download at least one subtitle corresponding to the specific visual content.

21. The method for adjusting the display state based on the environment as claimed in claim 13, further comprising:
when determining that the display mode of the display circuit is determined to be the first display mode in a plurality of predetermined display modes, controlling a microphone of the wearable device to receive a voice signal;
when determining that the voice signal indicates using a second display mode of the predetermined display modes as the display mode of the display circuit, controlling the display circuit to display a confirmation message, wherein the confirmation message comprises a first option and a second option respectively corresponding to the first display mode and the second display mode;
when determining that the first option is selected, controlling the display circuit to be adjusted to a display state corresponding to the first display mode; and
when determining that the second option is selected, controlling the display circuit to be adjusted to the display state corresponding to the second display mode.

22. The method for adjusting the display state based on the environment as claimed in claim 13, comprising: when determining that the at least one specific object corresponds to a first display mode in a plurality of predetermined display modes, determining the display mode of the display circuit to be the first display mode.

23. The method for adjusting the display state based on the environment as claimed in claim 22, wherein the predetermined display modes further comprise a second display mode, and the method further comprises:
when determining that the at least one specific object comprises at least one first object corresponding to the first display mode and at least one second object corresponding to the second display mode, obtaining a first quantity of the at least one first object and a second quantity of the at least one second object; and
when determining that the first quantity of the at least one first object is greater than the second quantity of the at least one second object, determining the display mode of the display circuit to be the first display mode; and
when determining that the first quantity of the at least one first object is less than the second quantity of the at least one second object, determining the display mode of the display circuit to be the second display mode.

\* \* \* \* \*